(12) United States Patent
Lin et al.

(10) Patent No.: US 10,856,823 B2
(45) Date of Patent: Dec. 8, 2020

(54) X-RAY DEVICE, ELECTRONIC DEVICE AND METHOD FOR OPERATING THE X-RAY DEVICE

(71) Applicant: Wistron Corp., New Taipei (TW)

(72) Inventors: Chih Kuan Lin, New Taipei (TW); Chen-An Sung, New Taipei (TW); Shih-An Chen, New Taipei (TW)

(73) Assignee: WISTRON CORP., New Taipei (TW)

( * ) Notice: Subject to any disclaimer, the term of this patent is extended or adjusted under 35 U.S.C. 154(b) by 84 days.

(21) Appl. No.: 16/007,193

(22) Filed: Jun. 13, 2018

(65) Prior Publication Data

US 2019/0209111 A1 Jul. 11, 2019

(30) Foreign Application Priority Data

Jan. 5, 2018 (TW) .............................. 107100458 A

(51) Int. Cl.
*A61B 6/00* (2006.01)
(52) U.S. Cl.
CPC .......... *A61B 6/4476* (2013.01); *A61B 6/4405* (2013.01); *A61B 6/4452* (2013.01); *A61B 6/589* (2013.01)
(58) Field of Classification Search
None
See application file for complete search history.

(56) References Cited

U.S. PATENT DOCUMENTS

2016/0206261 A1 7/2016 Lan et al.
2017/0236679 A1* 8/2017 Chaki ..................... H01J 35/26
378/131

FOREIGN PATENT DOCUMENTS

CN 104429055 A 3/2015

OTHER PUBLICATIONS

Intellectual Property Office Ministry of Economic Affairs, R.O.C., Office Action, dated Jul. 17, 2018, Taiwan.

* cited by examiner

*Primary Examiner* — Hoon K Song
(74) *Attorney, Agent, or Firm* — Locke Lord LLP; Tim Tingkang Xia, Esq.

(57) ABSTRACT

An X-ray device includes a casing, an X-ray generator, a zoom ring-like object and an elastic connecting assembly. The casing has a storage space. The X-ray generator is disposed on the casing and located in the storage space. One end of the zoom ring-like object is connected to the X-ray generator. One end of the elastic connecting assembly is connected to the X-ray generator or the zoom ring-like object, and another end of the elastic connecting assembly is connected to the casing, such that the zoom ring-like object or both the zoom ring-like object and the X-ray generator are inclinable relative to the casing.

16 Claims, 9 Drawing Sheets

X-RAY DEVICE, ELECTRONIC DEVICE AND METHOD FOR OPERATING THE X-RAY DEVICE

CROSS-REFERENCE TO RELATED APPLICATIONS

This non-provisional application claims priority under 35 U.S.C. § 119(a) on Patent Application No(s). 107100458 filed in Taiwan, R.O.C. on Jan. 5, 2018, the entire contents of which are hereby incorporated by reference.

TECHNICAL FIELD

The disclosure relates to an image capturing device and a method for operating the same, more particularly to an X-ray device, an electronic device and a method for operating the X-ray device.

BACKGROUND

X-rays have a strong penetrating power to objects. However, high dense tissues of a human body (e.g., bones) can absorb more X-rays and thus reduce the amount of the X-rays reaching an X-ray film, thereby leaving shadows on the X-ray film. As such, when taking an X-ray shot, there are dark and light shadows on the X-ray film due to different densities of human tissues. Owing to the property of X-rays, X-ray imaging has become an essential detection technique in medical diagnostic field. Recently, X-ray devices are widely used in dental, orthopedic and thoracic practices to see internal structures of human body and diagnose abnormalities. Medical X-ray devices may be designed in different sizes according to actual requirements. For example, there are stationary X-ray devices and handheld X-ray devices for meeting different requirements, such as imaging range, operability and the size of storage space. The handheld X-ray device has low radiation outputs (thus, being safer), easy operation and is low in price and small in size, so the handheld X-ray device is widely used in clinics, veterinary hospitals, local health centers and even school dispensaries.

SUMMARY

One embodiment of the disclosure provides an X-ray device, which includes a casing, an X-ray generator, a zoom ring-like object and an elastic connecting assembly. The casing has a storage space. The X-ray generator is disposed on the casing and located in the storage space. One end of the zoom ring-like object is connected to the X-ray generator. One end of the elastic connecting assembly is connected to the X-ray generator or the zoom ring-like object, and another end of the elastic connecting assembly is connected to the casing, such that the zoom ring-like object or both the zoom ring-like object and the X-ray generator are inclinable relative to the casing.

One embodiment of the disclosure provides an electronic device, and the electronic device includes a casing, an electronic assembly and an elastic connecting assembly. The casing has a storage space. The electronic assembly is disposed on the casing and located in the storage space. One end of the elastic connecting assembly is connected to the electronic assembly, and another end of the elastic connecting assembly is connected to the casing, such that the electronic assembly is inclinable relative to the casing.

One embodiment of the disclosure provides a method for operating an X-ray device, which includes measuring a plurality of pressures of the X-ray device by a plurality of pressure sensors when a zoom ring-like object of the X-ray device is pressed against an object to be imaged, determining an inclination direction of an X-ray generator relative to a casing according to the plurality of pressures and adjusting an inclination angle of the X-ray generator by a plurality of driving members and detecting a sensing information related to the zoom ring-like object and the object to be imaged and operating the plurality of driving members according to the sensing information.

BRIEF DESCRIPTION OF THE DRAWINGS

The present disclosure will become more fully understood from the detailed description given hereinbelow and the accompanying drawings which are given by way of illustration only and thus are not intending to limit the present disclosure and wherein.

DETAILED DESCRIPTION

Figure 1:
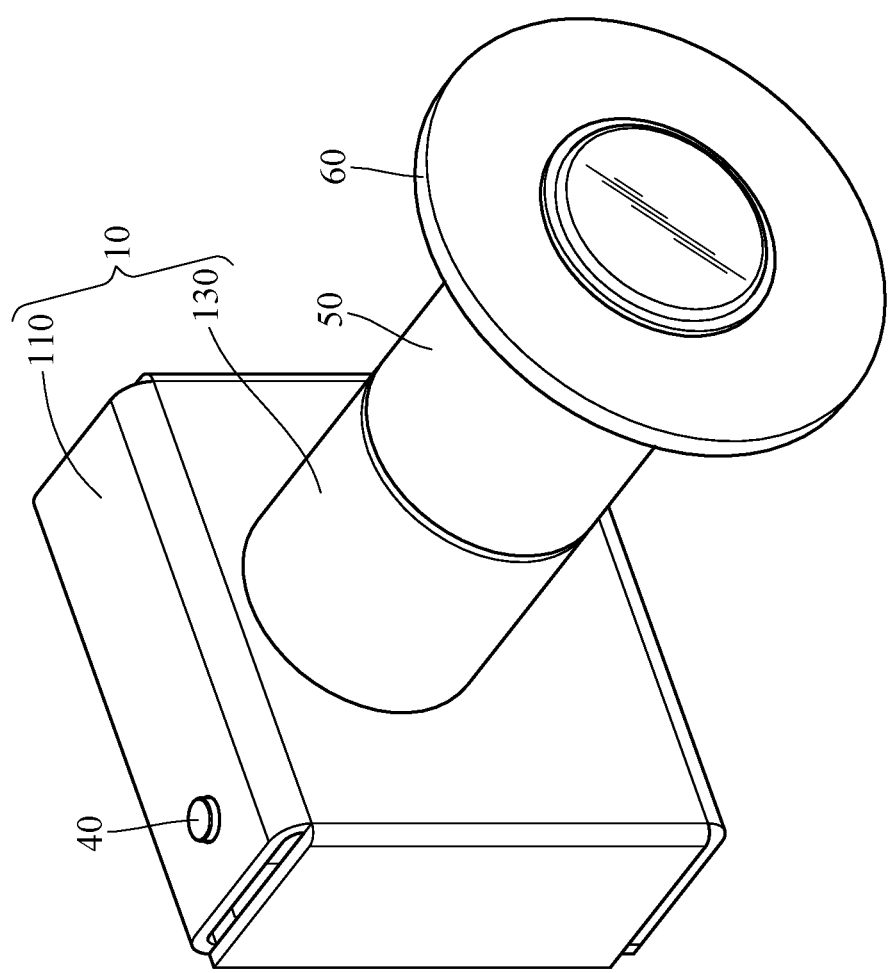
FIG. 1 is a perspective view of an X-ray device in accordance with a first embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
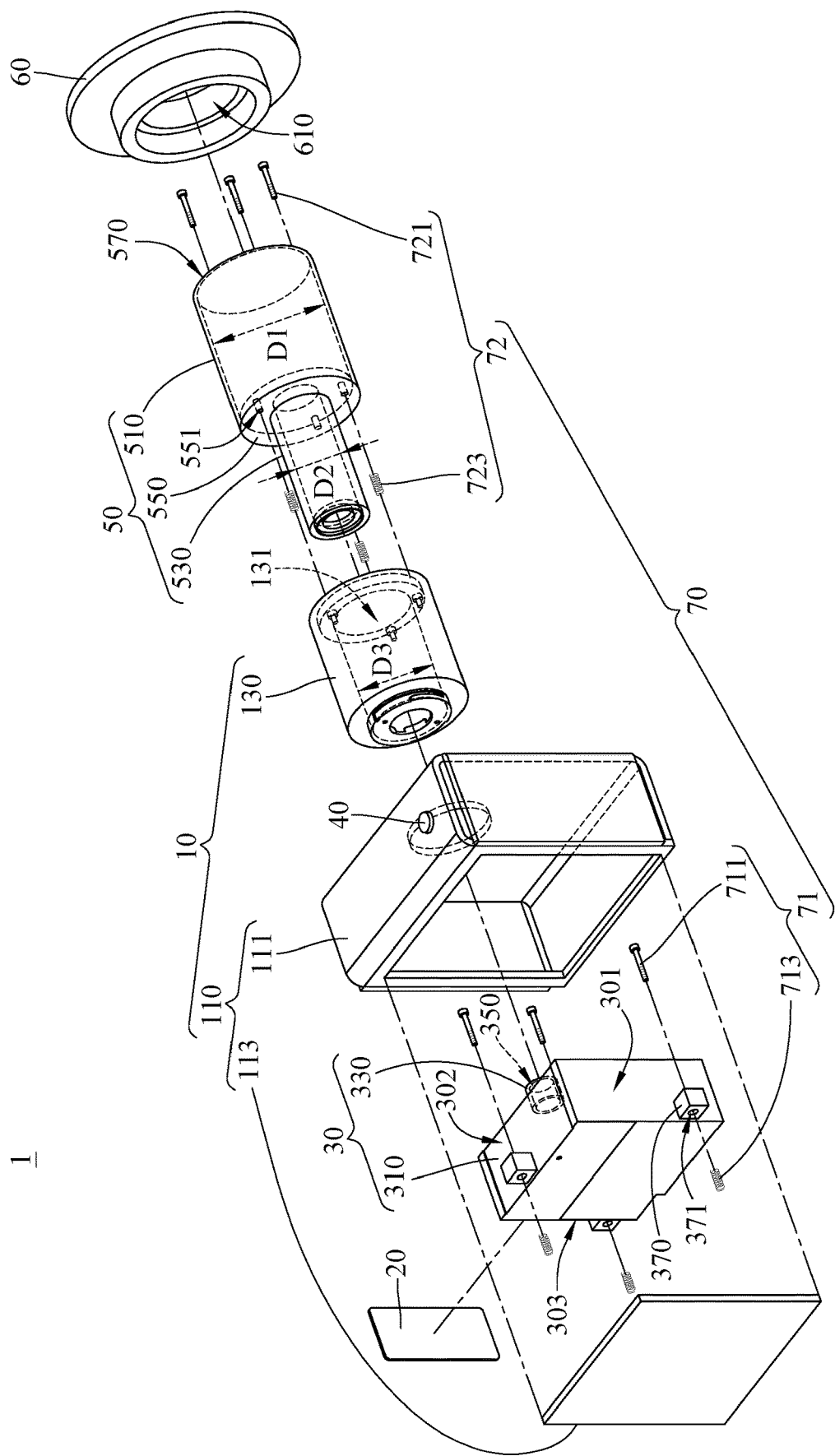
FIG. 2 is an exploded view of the X-ray device in FIG. 1.
Figure 3:
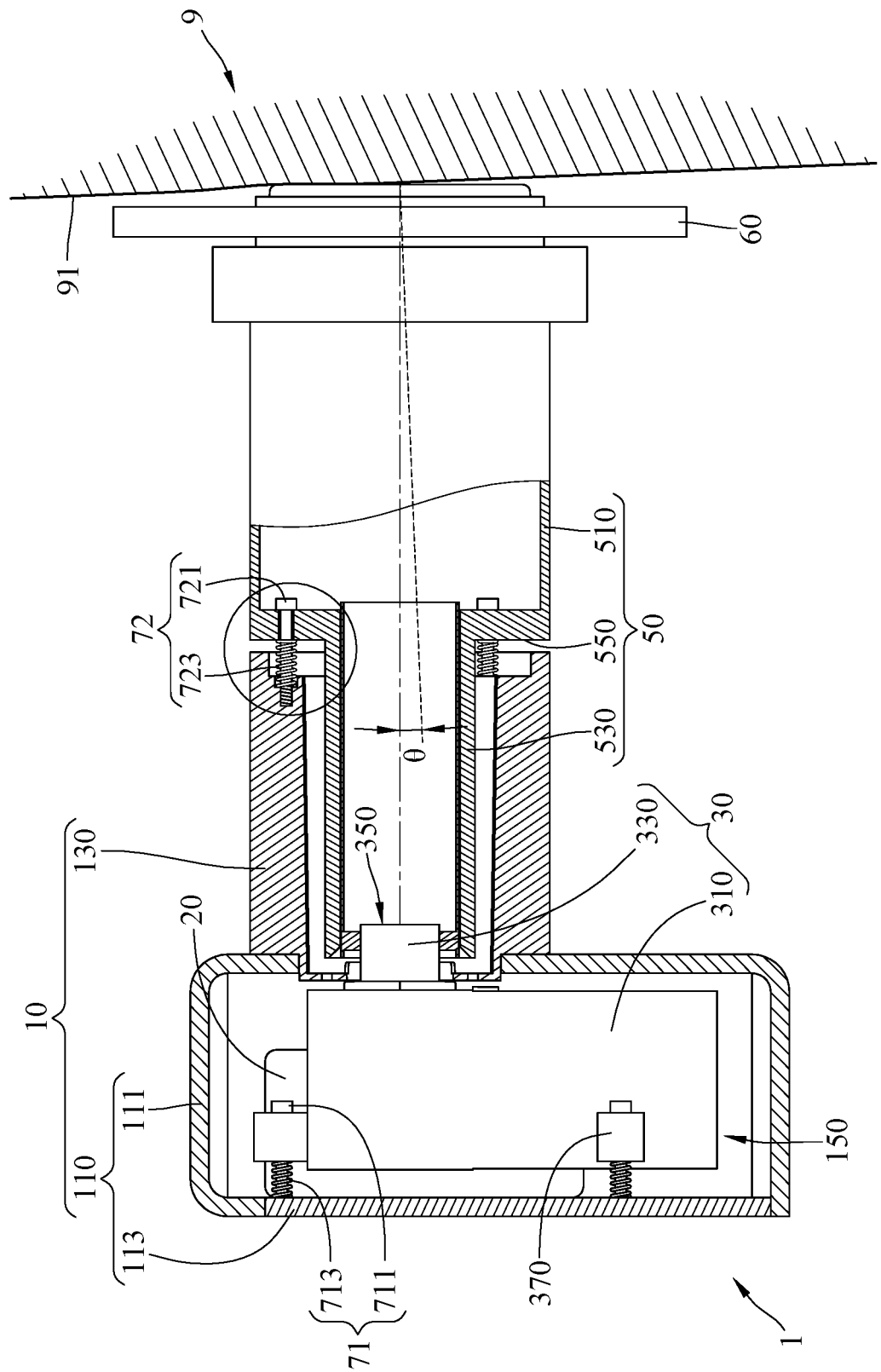
FIG. 3 is a cross-sectional view of the X-ray device in FIG. 1 and an object to be imaged.
Figure 4:
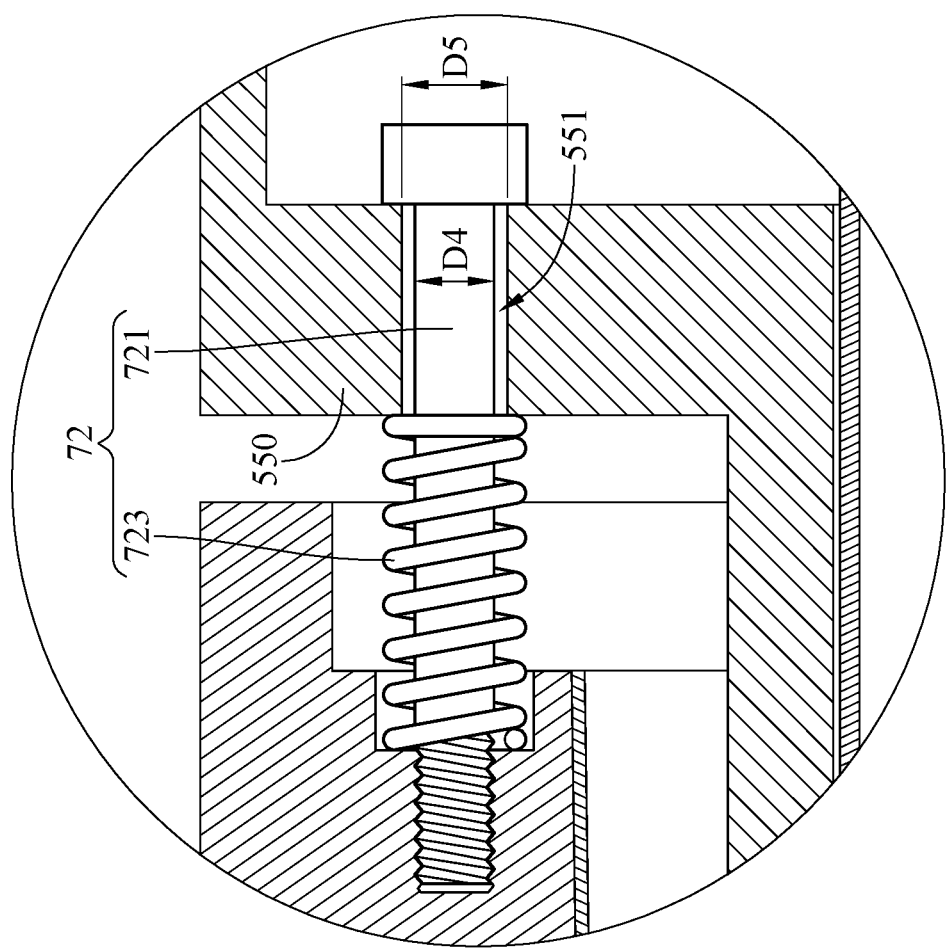
FIG. 4 is a partial enlarged view of the X-ray device in FIG. 3.

Please refer to FIG. 1 to FIG. 4. FIG. 1 is a perspective view of an X-ray device in accordance with a first embodiment of the present disclosure. FIG. 2 is an exploded view of the X-ray device in FIG. 1. FIG. 3 is a cross-sectional view of the X-ray device in FIG. 1 and an object to be imaged. FIG. 4 is a partial enlarged view of the X-ray device in FIG. 3.

In this embodiment, an X-ray device 1 is provided. The X-ray device 1 is a handheld X-ray device, but the present disclosure is not limited thereto. In other embodiments, the X-ray device 1 may be a stationary X-ray device. The X-ray device 1 includes a casing 10, a printed circuit board (PCB) 20, an X-ray generator 30, a shutter button 40, a zoom ring-like object 50, a contact member 60 and an elastic connecting assembly 70.

The casing 10 includes a main portion 110 and a cylindrical portion 130. The main portion 110 includes a front cover 111 and a back cover 113. The front cover 111 is disposed on the back cover 113. The cylindrical portion 130 protrudes from the front cover 111 of the main portion 110, and the cylindrical portion 130 and the main portion 110 together define a storage space 150. The cylindrical portion 130 has a bore 131, and the bore 131 is connected to the storage space 150. In this embodiment, the casing 10 includes the main portion 110 and the cylindrical portion 130, and the main portion 110 and the cylindrical portion 130 are two individual components, but the present disclosure is not limited thereto. In other embodiments, the casing may only have the main portion without the cylindrical portion, or the main portion and the cylindrical portion may be made of a single piece.

The PCB 20 and the X-ray generator 30 are both located in the storage space 150, and the X-ray generator 30 is disposed on the back cover 113 and electrically connected to the PCB 20. The X-ray generator 30 includes a base body 310, a collimator 330 and a light permeable portion 350 located on the collimator 330. The light permeable portion 350 corresponds to the bore 131 of the cylindrical portion 130.

The shutter button 40 is disposed on the front cover 111 and extends out of the casing 10. The shutter button 40 is electrically connected to the PCB 20. The shutter button 40 is able to control the X-ray generator 30 through the PCB 20.

The zoom ring-like object 50 is a hollow structure which includes a head portion 510, a neck portion 530 and a connecting portion 550, and the connecting portion 550 is connected to and located between the head portion 510 and the neck portion 530. An inner diameter D1 of the head portion 510 is larger than an inner diameter D2 of the neck portion 530, and the inner diameter D2 of the neck portion 530 is smaller than an inner diameter D3 of the cylindrical portion 130. The neck portion 530 of the zoom ring-like object 50 is disposed through the cylindrical portion 130 and is connected to the X-ray generator 30. The head portion 510 extends out of the casing 10, and the zoom ring-like object 50 has an opening 570 at an end of the head portion 510 away from the X-ray generator 30.

The contact member 60 covers the opening 570, and the contact member 60 has a penetration hole 610 corresponding to the opening 570 for light rays to pass through. In detail, the X-ray generator 30 emits X-rays from the light permeable portion 350 of the collimator 330, and then the X-rays sequentially travel through the neck portion 530, the head portion 510, the opening 570, and the penetration hole 610. On the other hand, exterior light rays are able to enter into the X-ray generator 30 in a backward direction.

The elastic connecting assembly 70 includes three first elastic connecting members 71 and three second elastic connecting members 72. The three first elastic connecting members 71 are respectively located at a first side 301, a second side 302 and a third side 303 of the X-ray generator 30; that is, the three first elastic connecting members 71 are respectively located at three different sides of the X-ray generator 30. The X-ray generator 30 is connected to the back cover 113 of the casing 10 through the first elastic connecting members 71. Each of the first elastic connecting members 71 includes a bolt 711 and an elastic member 713. The elastic member 713 is, for example, a spring. In this embodiment, the X-ray generator 30 further includes three fixing protrusions 370 respectively protruding from the first side 301, the second side 302 and the third side 303 of the base body 310. Each of the fixing protrusions 370 has a through hole 371. The bolt 711 is sequentially disposed through the through hole 371 and the elastic member 713 and then screwed to the back cover 113. As such, the three fixing protrusions 370 of the X-ray generator 30 are respectively pressed against the three elastic members 713 so that the X-ray generator 30 is inclinable relative to the casing 10.

Each of the second elastic connecting members 72 includes a bolt 721 and an elastic member 723. The elastic member 723 is, for example, a spring. In this embodiment, the connecting portion 550 of the zoom ring-like object 50 has three through holes 551. A diameter D4 of each bolt 721 is smaller than a diameter D5 of each through hole 551; that is, when the bolt 721 is disposed through the through hole 551, the bolt 721 is still movable. The bolt 721 is sequentially disposed through the through hole 551 and the elastic member 723 and then screwed to the cylindrical portion 130 of the casing 10. As such, the elastic members 723 are located between and pressed against by the connecting portion 550 and the cylindrical portion 130 so that the zoom ring-like object 50 is inclinable relative to the casing 10.

Figure 5:
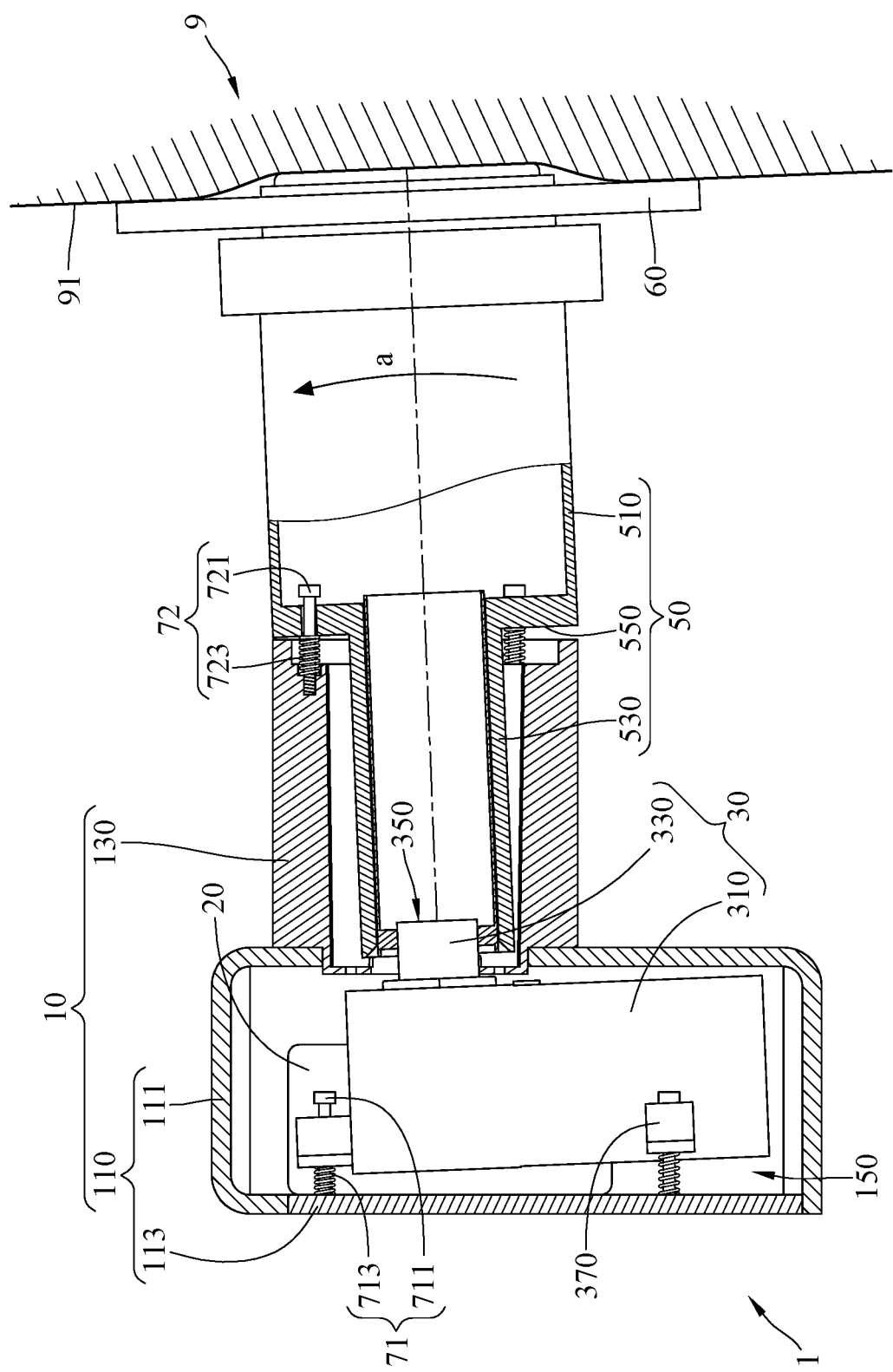
FIG. 5 is a cross-sectional view of the X-ray device in FIG. 1 when a zoom ring-like object of the X-ray device is pressed against the object to be imaged and inclined relative to a casing of the X-ray device.

As described above, the X-ray generator 30 and the zoom ring-like object 50 are inclinable relative to the casing 10 respectively through the first elastic connecting members 71 and the second elastic connecting members 72. Therefore, when the X-ray device 1 is attempted to image an object with a surface inclined with respect to the contact member 60, the X-ray device 1 can be pressed against the object to force the zoom ring-like object 50 to be inclined with respect to the casing 10 so as to help the contact member 60 to incline to contact with the surface of the object. As a result, the X-ray device 1 still can aim at the target area within the object. That is, the X-ray device 1 has a wide range of image capture, thus the X-ray device 1 is able to capture a clear image without increasing output power. In detail, please refer to FIG. 3 and FIG. 5, FIG. 5 is a cross-sectional view of the X-ray device in FIG. 1 when a zoom ring-like object of the X-ray device is pressed against the object to be imaged and inclined relative to a casing of the X-ray device. As shown in FIG. 3, the X-ray device 1 is about to image an object 9, the contact member 60 is not in flat contact with the object 9 because a surface 91 of the object 9 is uneven, and the X-ray device 1 cannot be turned due to some reasons (e.g., the casing 10 has an interference with part of the object 9 which is not shown in the figure, or the casing 10 is blocked by another object). To solve this, the X-ray device 1 can be moved forward to the object 9. By doing so, the casing 10 would apply a force on the contact member 60 to force it to rotate by an angle θ (e.g., rotated in a direction "a" as shown in FIG. 5), such that the contact member 60 and the zoom ring-like object 50 are inclined with respect to the casing 10, and the contact member 60 is in flat contact with the surface 91 of the object 9. As a result, the X-ray device 1 aims at the target area within the object 9.

It is worth to note that the X-ray generator 30, the zoom ring-like object 50 and contact member 60 are inclinable in various directions because the first elastic connecting members 71 are distributed around the X-ray generator 30 and the second elastic connecting members 72 are distributed around the zoom ring-like object 50. And this helps the zoom ring-like object 50 to contact an object in a desired manner whether the object has an uneven surface or is inclined with respect to the X-ray device 1.

In this embodiment, there are three first elastic connecting members and three second elastic connecting members, but the present disclosure is not limited to the quantity of the first elastic connecting member or the second elastic connecting member. In other embodiments, the quantity of the first elastic connecting members and the quantity of the second elastic connecting members may be two or more than four according to actual requirements.

In addition, in this embodiment, the three first elastic connecting members are respectively located at three different sides of the X-ray generator, but the present disclosure is not limited thereto. In other embodiments, the first elastic connecting members may be all located at the same side or located at two different sides of the X-ray generator.

Furthermore, in this embodiment, both the elastic members 713 and 723 are springs, but the present disclosure is not limited thereto. In other embodiments, both the elastic members may be rubbers, sponges or resilient hinges.

Moreover, the present disclosure is not limited to the configurations of the first elastic connecting members and the second elastic connecting members in the previous embodiments. For example, in other embodiments, each of the first elastic connecting members and each of the second elastic connecting members may only include the elastic member, and the elastic member may be a spring, a rubber, a sponge or a resilient hinge.

In addition, the second elastic connecting members in this embodiment are optional. In other embodiments, the X-ray device may not include the second elastic connecting members. In such a case, the zoom ring-like object is still can be inclined with respect to the casing because the zoom ring-like object can be moved along with the X-ray generator which is inclinable with respect to the casing.

It is noted that the present disclosure is not limited to the X-ray device. In other embodiments, any electronic device which has a configuration similar to that of the aforementioned X-ray device should fall within the scope of the present disclosure. For example, an electronic device includes a casing and an electronic assembly disposed in the casing, and the electronic assembly is connected to the casing by an elastic connecting assembly, such that the electronic assembly is inclinable relative to the casing.

Figure 6:
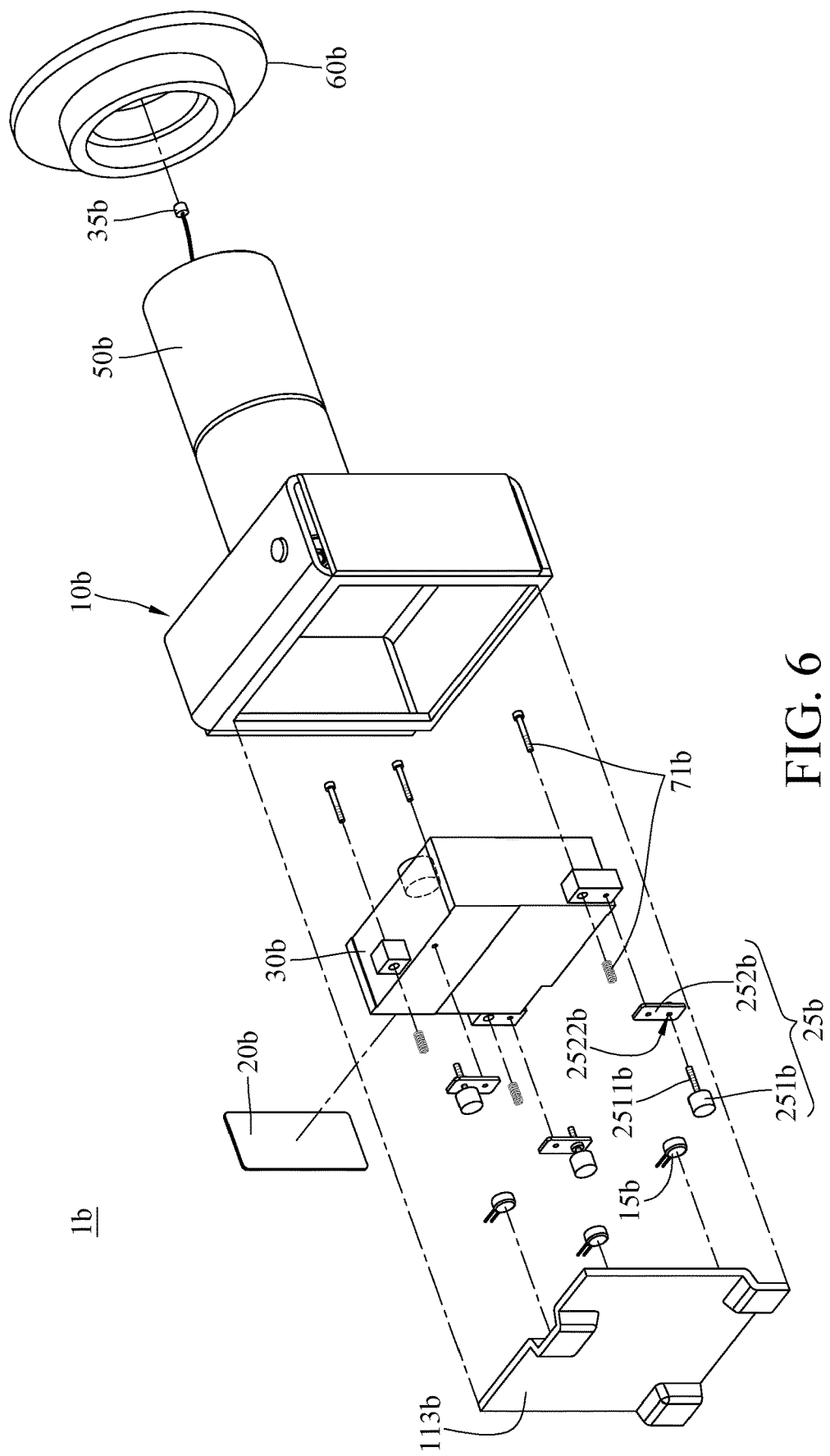
FIG. 6 is an exploded view of an X-ray device in accordance with a second embodiment of the present disclosure.
Figure 7:
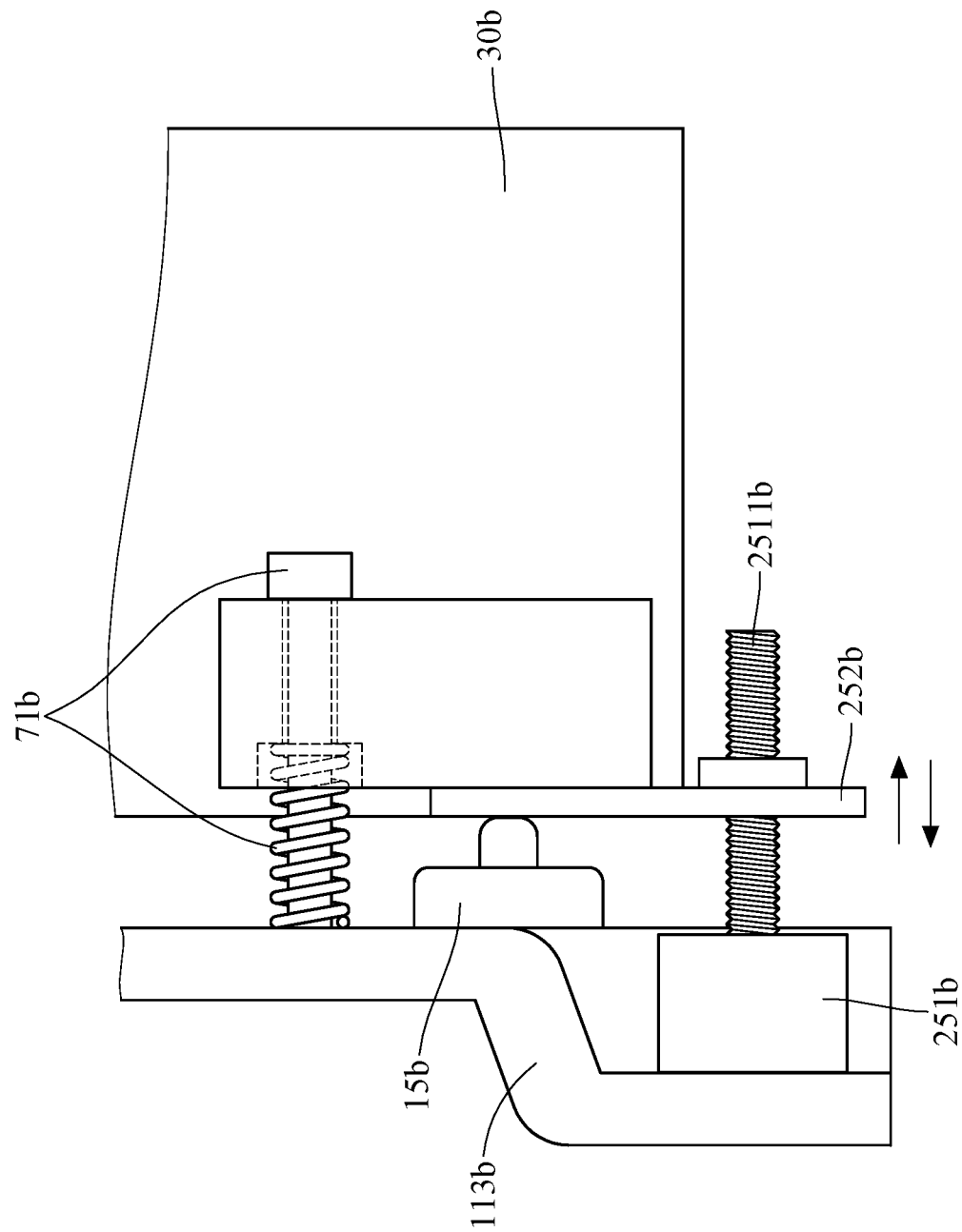
FIG. 7 is an enlarged view of pressure sensors and driving members in FIG. 6.

Then, please refer to FIG. 6 and FIG. 7. FIG. 6 is an exploded view of an X-ray device in accordance with a second embodiment of the present disclosure, and FIG. 7 is an enlarged view of pressure sensors and driving members in FIG. 6.

In this embodiment, an X-ray device 1*b* is provided. The differences between the X-ray device 1 and the X-ray device 1*b* are that the X-ray device 1*b* further includes three pressure sensors 15*b*, three driving members 25*b* and a sensor member 35*b* which are all electrically connected to a PCB 20*b*.

In this embodiment, the three pressure sensors 15*b* are disposed on a back cover 113*b* and respectively located next to three first elastic connecting members 71*b*. The pressure sensors 15*b* are in contact with an X-ray generator 30*b* and are configured to measure a pressure from the X-ray generator 30*b*.

The three driving members 25*b* are disposed on the back cover 113*b* and respectively located next to the three first elastic connecting members 71*b*. In this embodiment, each of the driving members 25*b* is, for example, an assembly including a micro-stepping motor and a screw rod. Each of the driving members 25*b* includes a motor 251*b* and a connecting plate 252*b*. The motors 251*b* are disposed on the back cover 113*b*, and each of the motors 251*b* has a screw rod 2511*b*. The connecting plates 252*b* are connected to the X-ray generator 30*b*, and each of the connecting plates 252*b* has a screw hole 2522*b*. The screw rods 2511*b* of the motors 251*b* are screwed into the screw holes 2522*b* of the connecting plates 252*b*, respectively. As shown in FIG. 7, when the screw rods 2511*b* are driven and rotated by the motors 251*b*, the connecting plates 252*b* are moved along axial directions of the screw rods 2511*b* by the screw rods 2511*b* interacting with the screw holes 2522*b* so as to adjust an inclination angle of the X-ray generator 30*b* with respect to the casing 10*b*. The driving members 25*b*, which are distributed around the X-ray generator 30*b*, are configured to push and pull different sides of the X-ray generator 30*b* so as to control the inclination angle of the X-ray generator 30*b*.

In addition, the present disclosure is not limited to the configuration of the driving member. For example, in other embodiments, the driving member may be a hydraulic motor.

The sensor member 35*b* is disposed on a contact member 60*b*, and the sensor member 35*b* is configured to measure a distance between the contact member 60*b* and an object to be imaged 9*b* (also can be called an object 9*b*). In this embodiment, the sensor member 35*b* is a thermal sensor, which is able to detect a temperature as a sensing information and use it to determine the distance between the contact member 60*b* and the object 9*b*, but the present disclosure is not limited thereto. In other embodiments, the sensor member may be a light sensor, a touch sensor or a proximity sensor to determine the distance between the contact member and the object through a different mean.

Figure 8:
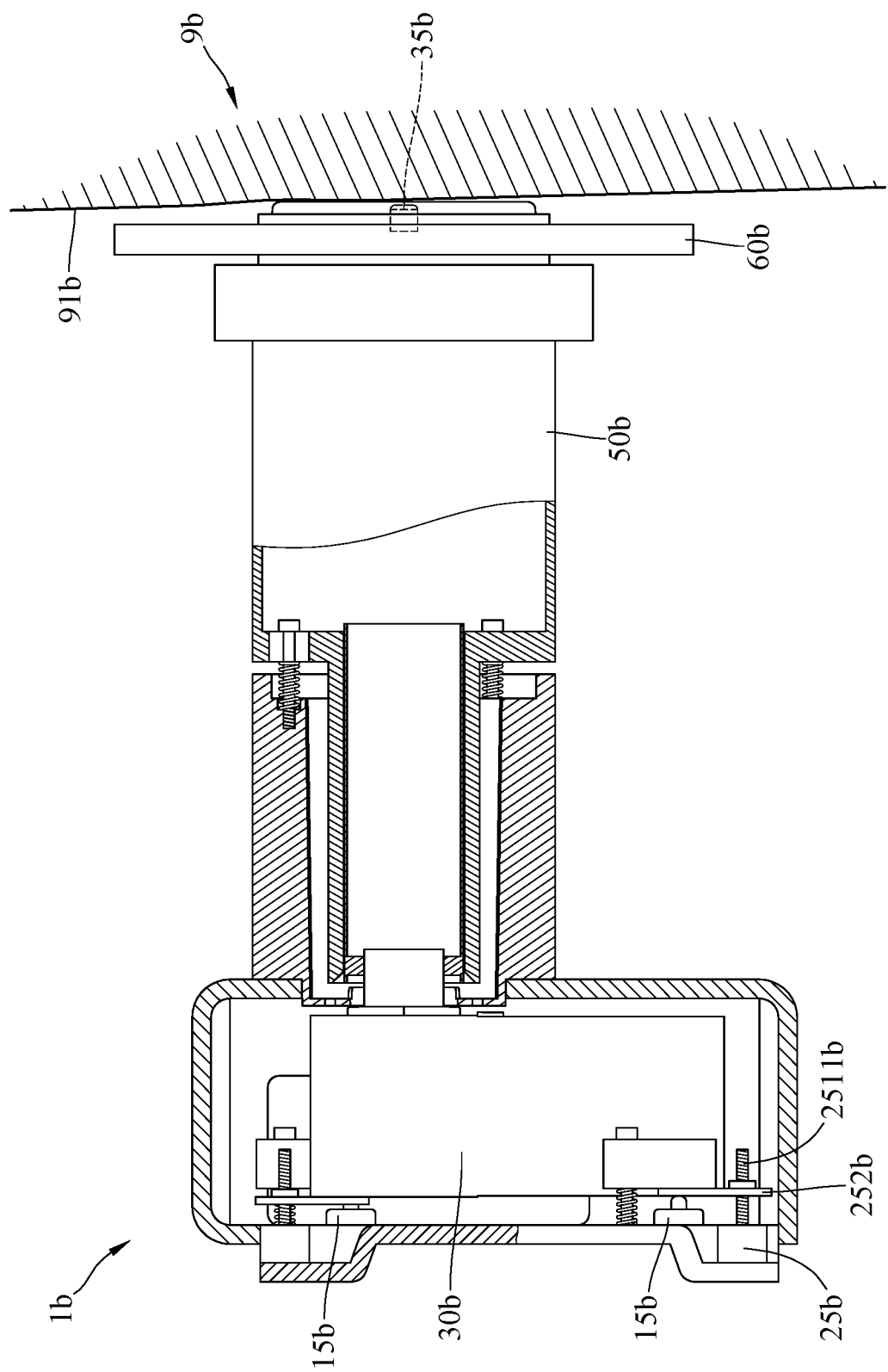
FIG. 8 is a cross-sectional view of the X-ray device in FIG. 6 and an object to be imaged.
Figure 9:
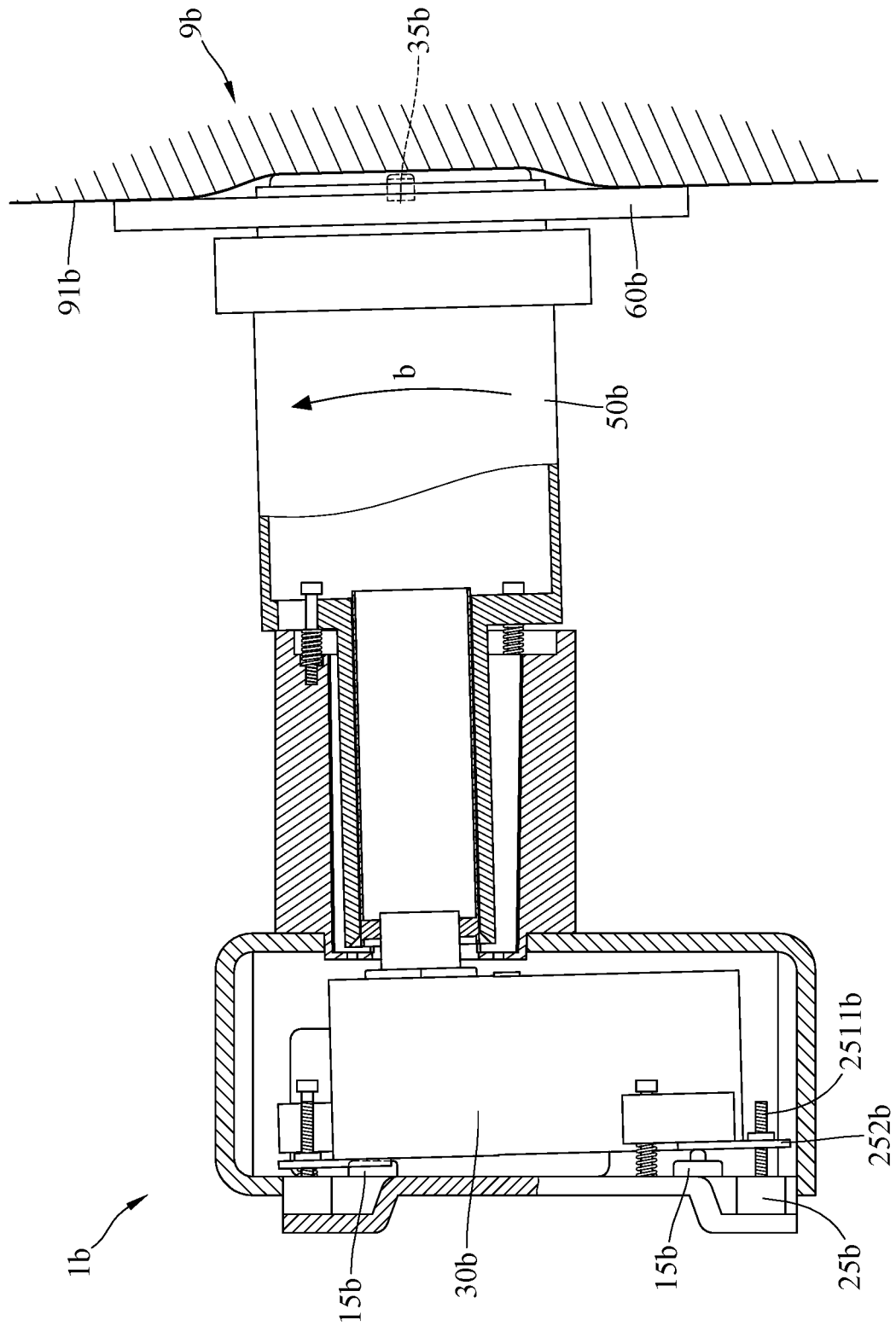
FIG. 9 is a cross-sectional view of the X-ray device in FIG. 6 when a zoom ring-like object of the X-ray device is pressed against the object to be imaged and inclined relative to a casing of the X-ray device.

In this embodiment, an inclination angle of a zoom ring-like object 50*b* is able to be automatically adjusted by the cooperation of the pressure sensors 15*b*, the driving members 25*b* and the sensor member 35*b*. In detail, please refer to FIG. 8 and FIG. 9. FIG. 8 is a cross-sectional view of the X-ray device in FIG. 6 and an object to be imaged, and FIG. 9 is a cross-sectional view of the X-ray device in FIG. 6 when a zoom ring-like object of the X-ray device is pressed against the object to be imaged and inclined relative to a casing of the X-ray device.

For example, as shown in FIG. 8, the contact member 60*b* is not in flat contact with the object 9*b* but pressed against the object 9*b* with its top portion because a surface 91*b* of the object 9*b* is uneven, and the X-ray device 1*b* cannot be turned due to some reasons (e.g., the casing 10*b* has an interference with part of the object 9*b* which is not shown in the figure, or the casing 10*b* is blocked by another object). As this moment, the pressure sensors 15*b* would measure a pressure from the X-ray generator 30*b* to determine an inclination direction of the X-ray generator 30*b*. In detail, the pressure sensor 15*b*, which is located at the same side as the side of the contact member 60*b* pressed against the object 9*b*, would measure a relatively large pressure than other pressure sensors 15*b*. It means that the X-ray generator 30*b* is inclined toward the same side as this pressure sensors 15*b*. After the inclination direction of the X-ray generator 30*b* is determined by the pressure sensors 15*b*, the driving members 25*b* respectively rotate the screw rods 2511*b* thereof so as to push or pull the sides of the X-ray generator 30*b* through the connecting plates 252*b*, such that the zoom ring-like object 50*b* can be rotated (e.g., in a direction "b") to be inclined relative to the casing 10*b* along with the movement of the X-ray generator 30*b*. During the movement of the X-ray generator 30*b*, the distance between the contact member 60*b* and the object 9*b* can be determined according to the temperature (the sensing information) obtained by the sensor member 35*b*. When the distance between the contact member 60*b* and the object 9*b* is determined in a predetermined range in a predetermined period of time, the contact member 60*b* is determined to be in flat contact with the surface 91*b* of the object 9*b*. Then, the driving members 25b stop operating, and the X-ray generator 30b is ready for capturing images of the object 9b. In the contrary, if the distance between the contact member 60b and the object 9b are not determined in the predetermined range during the predetermined period of time, the driving members 25b also stop operating, and then the X-ray device 1b would be relocated to a better position. Accordingly, since the inclination angle of the zoom ring-like object 50b is able to be automatically adjusted by the cooperation of the pressure sensors 15b, the driving members 25b and the sensor member 35b, the X-ray device 1b is able to automatically and precisely aim at the target area within the object 9b, and the effect of the manual force on the X-ray device 1b is minimized, thereby ensuring the image quality of the X-ray device 1b.

In addition, a further step can be performed before the aforementioned operation. In detail, before placing the X-ray device 1b on the object 9b, the sensor member 35b may be used to detect the temperature of the surface 91b of the object as a predetermined temperature to be a criterion for determining the distance between the contact member 60b and the object 9b. As such, the X-ray device 1b is applicable to various applications. For example, the X-ray device 1b is capable of capturing X-ray images of both cold-blooded and warm-blooded animals.

According to the X-ray device, the electronic device and the method for operating the X-ray device as described above, the X-ray generator and the zoom ring-like object are connected to the casing by the elastic connecting assembly, such that the X-ray generator and the zoom ring-like object are inclinable relative to the casing. Therefore, when the X-ray device is attempted to image an object with a surface inclined with respect to its contact member, the X-ray device can be pressed against the object to force the zoom ring-like object to be inclined with respect to the casing so as to help the contact member to incline to be in flat contact with the surface of the object. As a result, the X-ray device can aim at the target area within the object, and the X-ray device is able to capture a clear image without increasing output power.

Furthermore, since the inclination angle of the zoom ring-like object is able to be automatically adjusted by the cooperation of the pressure sensors, the driving members and the sensor member, the X-ray device is able to automatically and precisely aim at the target area within the object, and the effect of the manual force on the X-ray device is minimized, thereby ensuring the image quality of the X-ray device.

The embodiments were chosen and described in order to best explain the principles of the disclosure and its practical applications, to thereby enable others skilled in the art to best utilize the disclosure and various embodiments with various modifications as are suited to the particular use contemplated. It is intended that the scope of the disclosure be defined by the following claims and their equivalents.

What is claimed is:

1. An X-ray device, comprising:
   a casing, having a storage space;
   an X-ray generator, disposed on the casing and located in the storage space;
   a zoom ring-like object, one end of the zoom ring-like object being connected to the X-ray generator; and
   an elastic connecting assembly, wherein one end of the elastic connecting assembly is connected to the X-ray generator or the zoom ring-like object, and another end of the elastic connecting assembly is connected to the casing, such that the zoom ring-like object or both the zoom ring-like object and the X-ray generator are inclinable relative to the casing.

2. The X-ray device according to claim 1, wherein the elastic connecting assembly comprises a plurality of first elastic connecting members respectively located at sides of the X-ray generator; one end of each of the plurality of first elastic connecting members is connected to the X-ray generator, and another end of each of the plurality of first elastic connecting members is connected to the casing, such that the X-ray generator is inclinable relative to the casing.

3. The X-ray device according to claim 2, wherein the casing further has a bore connected to the storage space, the X-ray generator has a light permeable portion corresponding to the bore, and another end of the zoom ring-like object is disposed through the bore and extends out of the casing.

4. The X-ray device according to claim 3, wherein the elastic connecting assembly comprises a plurality of second elastic connecting members, the zoom ring-like object comprises a head portion, a neck portion and a connecting portion connecting, the connecting portion is connected to and located between the head portion and the neck portion, and the neck portion is connected to the X-ray generator; a first end of each of the plurality of second elastic connecting members is connected to the connecting portion, and a second end of each of the plurality of second elastic connecting members is connected to the casing, such that the zoom ring-like object is inclinable relative to the casing.

5. The X-ray device according to claim 4, wherein the head portion extends out of the casing, and an inner diameter of the head portion is larger than an inner diameter of the neck portion.

6. The X-ray device according to claim 4, wherein the casing further comprises a main portion and a cylindrical portion, the cylindrical portion protrudes from the main portion, the cylindrical portion and the main portion together form the storage space, the bore is located at the cylindrical portion, the second ends of the plurality of second elastic connecting members are connected to the cylindrical portion.

7. The X-ray device according to claim 6, wherein the main portion and the cylindrical portion are made of a single piece.

8. The X-ray device according to claim 6, wherein an inner diameter of the neck portion is smaller than an inner diameter of the cylindrical portion, and the neck portion is disposed through the cylindrical portion and connected to the X-ray generator.

9. The X-ray device according to claim 2, wherein the plurality of first elastic connecting members are springs, rubbers, sponges or resilient hinges.

10. The X-ray device according to claim 2, wherein each of the plurality of first elastic connecting members comprises a bolt and an elastic member, and the X-ray generator has a plurality of through holes; the bolts are respectively disposed through the plurality of through holes and the elastic members and are screwed to the casing, such that the X-ray generator is pressed against the elastic members and thereby inclinable relative to the casing.

11. The X-ray device according to claim 10, wherein the plurality of elastic members are springs, rubbers, sponges or resilient hinges.

12. The X-ray device according to claim 1, further comprising a plurality of pressure sensors and a plurality of driving members, respectively located at sides of the X-ray generator, wherein the plurality of pressure sensors are fixed in the storage space and in contact with the X-ray generator, the plurality of driving members are disposed on the casing and located in the storage space, the plurality of pressure sensors are configured to measure a pressure from the X-ray generator to determine an inclination direction of the X-ray generator, and the plurality of driving members are configured to control an inclination angle of the X-ray generator.

13. The X-ray device according to claim 12, further comprising a contact member and a sensor member, wherein the contact member covers an opening of the zoom ring-like object away from the X-ray generator, the sensor member is disposed on the contact member, and the sensor member is configured to measure a distance between the contact member and an object to be imaged.

14. The X-ray device according to claim 13, wherein the sensor member is a light sensor, a thermal sensor, a touch sensor or a proximity sensor.

15. The X-ray device according to claim 12, wherein each of the plurality of driving members comprises a motor and a connecting plate, the motors are disposed on the casing, and each of the motors has a screw rod, the connecting plates are connected to the X-ray generator, each of the connecting plates has a screw hole, the screw rods are respectively threaded into the screw holes; when the screw rods are driven and rotated by the motors, the connecting plates are moved along axial directions of the screw rods by the screw rods interacting with the screw holes so as to adjust the inclination angle of the X-ray generator with respect to the casing.

16. A method for operating an X-ray device, comprising:
measuring a plurality of pressures of the X-ray device by a plurality of pressure sensors when a zoom ring-like object of the X-ray device is pressed against an object to be imaged;
determining an inclination direction of an X-ray generator relative to a casing according to the plurality of pressures and adjusting an inclination angle of the X-ray generator by a plurality of driving members; and
detecting a sensing information related to the zoom ring-like object and the object to be imaged and operating the plurality of driving members according to the sensing information.

* * * * *